United States Patent [19]

Gruber

[11] 4,420,597

[45] Dec. 13, 1983

[54] (METH)ACRYLATES OF ISOCYANURIC ACID DERIVATIVES CONTAINING HYDROXYL GROUPS AND THEIR USE AS ADHESIVES

[75] Inventor: Werner Gruber, Korschenbroich, Fed. Rep. of Germany

[73] Assignee: Henkel Kommanditgesellschaft auf Aktien, Düsseldorf-Holthausen, Fed. Rep. of Germany

[21] Appl. No.: 306,777

[22] Filed: Sep. 29, 1981

[30] Foreign Application Priority Data

Nov. 25, 1980 [DE] Fed. Rep. of Germany ....... 3044318

[51] Int. Cl.³ ............................................ G08F 20/26
[52] U.S. Cl. ................................................ 526/261
[58] Field of Search ........................................ 526/261

[56] References Cited

U.S. PATENT DOCUMENTS

| | | | |
|---|---|---|---|
| 3,061,591 | 10/1962 | Roth | 526/261 |
| 3,293,248 | 12/1966 | Sheffer | 544/221 |
| 3,297,785 | 1/1967 | George et al. | 544/221 |
| 3,332,946 | 7/1967 | Little | 526/261 |
| 3,658,801 | 4/1972 | Berry et al. | 526/261 |

Primary Examiner—Harry Wong, Jr.
Attorney, Agent, or Firm—Hammond & Littell, Weissenberger & Muserlian

[57] ABSTRACT

This invention is directed to esters of isocyanuric acid derivatives. More particularly, this invention is directed to acrylates or methacrylates of isocyanuric acid derivatives containing hydroxyl groups, the preparation of said compounds, and their use in adhesives.

8 Claims, No Drawings

(METH)ACRYLATES OF ISOCYANURIC ACID DERIVATIVES CONTAINING HYDROXYL GROUPS AND THEIR USE AS ADHESIVES

FIELD OF THE INVENTION

This invention is directed to esters of isocyanuric acid derivatives. More particularly, this invention is directed to acrylates or methacrylates of isocyanuric acid derivatives containing hydroxyl groups, the preparation of said compounds, and their use in adhesives.

OBJECTS OF THE INVENTION

It is an object of the invention to provide (meth)acrylates of isocyanuric acid derivatives containing hydroxyl groups.

It is also an object of the invention to provide a method of preparing said compounds.

It is a further object of the invention to provide adhesive compositions based upon said compounds.

These and other objects of the invention will become more apparent in the discussion below.

DETAILED DESCRIPTION OF THE INVENTION

The present invention is directed to acrylates or methacrylates of isocyanuric acid containing hydroxyl groups, said compounds having the formula $$\text{(I)}$$

wherein R is hydrogen, methyl, or ethyl, and each $R^1$ is a member selected from the group consisting of (1) members selected from the group consisting of (a) —OH;

(b) $-O-\underset{\underset{O}{\|}}{C}-\underset{\underset{}{|}}{C}(CH_3)=CH_2$; and (II)

(c) $-O-\underset{\underset{O}{\|}}{C}-CH=CH_2$, (III)

and (2) members selected from the group consisting of (d) $-O-\underset{\underset{O}{\|}}{C}-CH=CH-\underset{\underset{O}{\|}}{C}-OH$; (IV)

(e) $-O-\underset{\underset{O}{\|}}{C}-CH=CH-\underset{\underset{O}{\|}}{C}-O-CH_2-\underset{\underset{OH}{|}}{CH}-CH_2-O-\underset{\underset{O}{\|}}{C}-\underset{\underset{}{|}}{C}(CH_3)=CH_2$; (V)

and (f) $-O-\underset{\underset{O}{\|}}{C}-CH=CH-\underset{\underset{O}{\|}}{C}-O-CH_2-\underset{\underset{OH}{|}}{CH}-CH_2-O-\underset{\underset{O}{\|}}{C}-CH=CH_2$, (VI)

with the proviso that only one $R^1$ can be —OH or a radical of Formula III, IV, or VI.

It is known that cyanuric acid and alkylene oxides readily yield the respective isocyanurates with the formation of an active hydroxyl group in α-position, said isocyanurates having the formula $$\text{(VII)}$$

wherein R varies according the alkylene oxide used. In the present case, R is hydrogen, methyl, or ethyl. Thus, trihydroxy($C_2$-$C_4$)alkyl isocyanurates of Formula VII are used for the preparation of the compounds according to the invention.

Starting with the compounds of Formula VII, the hydroxyl groups can be esterified either directly with methacrylic acid under well-known conditions or the methacrylic acid radical can be introduced with methacrylic acid chloride in the presence of suitable solvents, such as dimethylformamide or similar compounds. When the acrylic acid radical is to be partially introduced, this can be accomplished with the respective substitution of methacrylic acid or its chloride by acrylic acid or its chloride.

Furthermore, starting from the compounds of Formula VII, the hydroxyl groups can be converted into the partial esters with free carboxyl groups by the use of maleic anhydride. These partial esters are then changed into the tri-(meth)acrylates of Formulas IV, V, and VI by reaction with glycidyl methacrylate, which can, if desired, be replaced by glycidyl acrylate in an amount of up to one third. When up to one third less glycidyl (meth)acrylate, based on molar ratios, is used, compounds are obtained that still contain free carboxyl groups and mainly consist of di-(meth)acrylate derivatives of trihydroxyalkyl isocyanuric acid.

The methacrylates of Formula I according to the invention are monomers that can be converted into high molecular weight compounds with the aid of known initiators. They are advantageously used as components of acrylate adhesives that harden under the exclusion of oxygen. Particularly heat-resistant bonds can be obtained with the use of the esters according to the invention. They are distinctly superior to adhesive mixtures based upon dimethacrylates from propoxylated diphenylol propane.

The adhesives according to the invention also may contain up to 50 percent by weight of additional polymerizable components, for example, monomethacrylates such as tetrahydrofurfuryl methacrylate, 5,6-dihydrodicyclopentadienyl methacrylate, cyclohexyl methacrylate, ethylhexyl methacrylate, hydroxyethyl methacrylate, hydroxypropyl methacrylate, or di-methacrylates such as ethylene glycol dimethacrylate, triethylene glycol dimethacrylate, or polyethylene glycol dimethacrylate. As initiators, the adhesives and sealing materials contain peroxides, especially hydroperoxides such as cumene hydroperoxide, tert.butylhydroperoxide, methylethyl-ketone-hydroperoxide, or diisopropyl-benzene-hydroperoxide. These are generally added in amounts of from about 0.1 to 20, preferably from about 1 to 10. percent by weight, based on the weight of the polymerizable contents.

The adhesives or sealers according to the invention may contain one or more customary adjuvant substances selected from the group consisting of stabilizers, accelerators, plasticizers, inorganic fillers, thickeners, and dyes for certain applications.

Stabilizers and accelerators are advantageously added to the adhesives and sealing agents according to the invention. Suitable stabilizers include quinone or hydroquinone in concentrations of from about 100 to 1000 ppm, preferably from about 200 to 500 ppm, based upon the polymerizable contents. Suitable accelerators include the so-called imide accelerators such as benzoic acid sulfimide, and particularly sulfohydrazide accelerators, such as p-toluene sulfonic acid hydrazide, in combination with a tert.amine, preferably N,N-dimethyl-p-toluidine. Accelerators and stabilizers must be added in mutually adjusted proportions to obtain optimal properties for the adhesives or sealers. They are each generally added in amounts of from about 0.1 to 3 percent by weight, based upon the total weight of the polymerizable contents.

Especially suitable as thickeners for increased viscosity are polymeric compounds such as polymethyl methacrylate, polyethyl acrylate, polystyrene, polyvinyl chloride, synthetic rubber, and the like. Suitable fillers include, for example, finely-divided silicon dioxide, silicates, bentonites, calcium carbonate, and titanium dioxide.

The adhesives or sealers are prepared by mixing the components at room temperature. The resulting adhesives or sealers can remain stable for months or even years provided they are either stored in containers that admit air, such as polyethylene bottles, or are stored in bottles of glass or the like that are partly filled with air. A relatively low oxygen partial pressure suffices to inhibit polymerization. It has been found expedient to use colored bottles which prevent passage of short-wave light. The stability of the compounds is therefore favorably influenced. Stabilization can also be achieved in known manner by the addition of organic peracids, such as peracetic acid.

Small quantities of the adhesive compositions are introduced between the surfaces to be bonded, after which the surfaces are contacted with each other sufficiently firmly or in another manner so as to exclude air or oxygen. Then the compositions of the invention polymerize to rapidly form a firm bond. It is naturally also possible to accelerate the hardening with known means, as, for example, by heating the areas to be adhered.

Advantages of the adhesives or sealers obtainable according to the invention are, among others, mainly that the parts to be bonded can be laminated at room temperature and that a load can be placed on them after a short time.

The heat resistance of such laminations is generally excellent. Consequently, the adhesives according to the invention are suited for the bonding of metals, particularly when great strength with good heat stability of the glued joint is required. Thus they are used in industry for the gluing of metal sheets or materials of different metals, for the attaching of bearing shafts, for the sealing of pipe joints, and for similar jobs. It is noteworthy that, with adhesive compositions according to the invention, there is only a slight decrease in strength between 100° C. and 150° C., as shown in the examples below. Even at 200° C., almost 50 percent of the torque measured at room temperature, was observed.

The following examples are intended to illustrate the invention and should not be construed as limiting the invention thereto.

EXAMPLES

EXAMPLE 1

Trimethacryloylethyl isocyanurate

One hundred seventy-five grams (0.67 mol) of trihydroxyethyl isocyanurate were dissolved in 200 ml of dimethylformamide and reacted at approximately 5° C. with 208 gm (2 mols) of methacrylic acid chloride in the presence of 202 gm (2 mols) of triethylamine. The reaction mixture was then heated at 50° C. for one hour. The reaction batch was poured into water, and the trimethacrylate was taken up in methylene chloride. A yellow-brown, viscous oil remained after drying and evaporation of the solvent.

Yield: 250 gm (81% of theory).
Analysis: Calc.: C 54.19, H 5.81, N 9.03; Found: C 54.00, H 5.35, N 9.23.
M.p.: 65° C.

EXAMPLE 2

Bismethacryloylethyl-hydroxyethyl isocyanurate

One hundred seventy-five grams (0.67 mol) of trihydroxyethyl isocyanurate were dissolved in 200 ml of dimethylformamide and reacted at approximately 5° C. in the presence of 131 gm (1.3 mol) of triethylamine and 135 gm (1.3 mol) of methacrylic acid chloride. The reaction mixture was worked up analogously to the procedure described in Example 1.

Yield: 240 gm (80% of theory).
Analysis: Calc.: C 51.39, H 5.79, N 10.58; Found: 51.70, 6.16, 10.20.
$n_D^{20}$: 1.5107.

EXAMPLE 3

Triglycidyl methacrylate of the maleic acid partial ester of trihydroxyethyl isocyanurate Three hundred ninety-two grams (1.5 mol) of trihydroxyethyl isocyanurate and 441 gm (4.5 mols) of maleic anhydride were reacted at 100° C. until the acid number was 315 (calc.: 302). Then, the reaction mixture was reacted with 639 gm (4.5 mols) glycidyl methacrylate at 80° C. The acid number was 10 after 10 hours.

Yield: 1472 gm (100% of theory).
Analysis: Calc.: C 51.06, H 5.78, N 4.26; Found: 50.50, 5.37, 4.30.
$n_D^{20}$: 1.521.

EXAMPLE 4

Diglycidyl methacrylate of the maleic acid partial ester of trihydroxyethyl isocyanurate The partial ester was prepared using a procedure analogous to that described in Example 3. The methacryloylation was carried out at 80° C. with 425 gm (3 mols) of glycidyl methacrylate to an acid number of 110 (calc.: 101).

Yield: 1258 gm (100% of theory).

Analysis: Calc.: C 49.93, H 5.77, N 5.64; Found: 50.00, 5.28, 5.23.

$n_D^{20}$: 1.533.

EXAMPLE 5

Adhesive mixture of dimethacrylates and trimethacrylates

Fifty gm of each of the dimethacrylates or trimethacrylates of Examples 1 to 4 were diluted with 20 gm of hydroxyethyl methacrylate and 20 gm of triethylene glycol dimethacrylate. These monomer mixtures were mixed with 5 gm of polymethylmethacrylate, 1 gm of p-toluene sulfonic acid hydrazide, 3 gm of cumene hydroperoxide, and 1 gm of triethylamine. The resulting anaerobic adhesives were tested for their properties. The stability, measured in the conventional 80° C. temperature test, was above 30 minutes for all mixtures. For this purpose, a test tube 10 cm long and 10 mm wide was filled to 9/10 with a mixture according to one of Examples 1 to 4, immersed in a bath maintained at 80° C., and observed until the gel formation began. The accelerated aging test was not pursued since this test means that the products must be stable for approximately one year at room temperature.

Screws (M 10×30 DIN 933-8.8) and nuts (M 10 DIN 934-5.6) were glued together and then clamped in a vise after three days of aging, and the torque was determined with a torque meter. The compressive shear strength was determined at room temperature with glued boxes of steel ST 50 K (height 10 mm, diameter 20 mm) and pins of steel ST 50 K (length 10 mm, diameter 19.85 mm) after storing (24 hours), at room temperature (DIN-Entwurf 54 452).

The compressive shear strength after 1 day was determined in an additional test with test specimens heated to 180° C. for 3 hours. The heating was accomplished in a heating cabinet for the indicated time, and the testing was performed immediately after removal from the heating cabinet. All tests were carried out five times and the mean of the test results was recorded. The determined values are compiled in the following table:

TABLE

| Adhesive mixture according to Example No. | Torque after 3 hours (Nm) | Compressive Shear Strength after 24 hours (N/mm²) | Compressive Shear Strength after 24 hours/20° C. and 3 hours/180° C. (N/mm²) |
|---|---|---|---|
| 1 | 30 | 33 | 25 |
| 2 | 35 | 35 | 25 |
| 3 | 50 | 33 | 15 |
| 4 | 40 | 31 | 15 |

Comparison Test

In accordance with the procedure set forth in Example 5, the dimethacrylate of the reaction product of 2 mols of propylene oxide and 1 mol of diphenyl propane was mixed with the additives mentioned in Example 5. Then, the tests described therein were performed. Compressive shear strength after 24 hours: 35 N/mm²; compressive shear strength at 180° C.: 10 N/mm².

The preceding specific embodiments are illustrative of the practice of the invention. It is to be understood, however, that other expedients known to those skilled in the art or disclosed herein, may be employed without departing from the spirit of the invention or the scope of the appended claims.

I claim:

1. An anaerobically hardening adhesive and sealing composition comprising one or more compounds of the formula $$
\begin{array}{c}
R \quad\quad\quad O \quad\quad\quad R \\
| \quad\quad\quad || \quad\quad\quad | \\
H-C-CH_2-N \quad\quad N-CH_2-CH \\
| \quad\quad\quad\quad\quad\quad\quad\quad\quad | \\
R^1 \quad O \quad N \quad O \quad R^1 \\
\quad\quad\quad | \\
\quad\quad\quad CH_2 \\
\quad\quad\quad | \\
\quad\quad R-C-R^1 \\
\quad\quad\quad | \\
\quad\quad\quad H
\end{array}
\tag{I}
$$

wherein R is hydrogen, methyl, or ethyl, and each $R^1$ is a member selected from the group consisting of (1) members selected from the group consisting of (a) —OH;

(b) $-O-\underset{\underset{O}{||}}{C}-\underset{\underset{}{|}}{\overset{CH_3}{C}}=CH_2$; and (II)

(c) $-O-\underset{\underset{O}{||}}{C}-CH=CH_2$. (III)

and (2) members selected from the group consisting of (d) $-O-\underset{\underset{O}{||}}{C}-CH=CH-\underset{\underset{O}{||}}{C}-OH$; (IV)

(e) $-O-\underset{\underset{O}{||}}{C}-CH=CH-\underset{\underset{O}{||}}{C}-O-CH_2-\underset{\underset{OH}{|}}{CH}-CH_2-O-\underset{\underset{O}{||}}{C}-\underset{\underset{}{|}}{\overset{CH_3}{C}}=CH_2$; (V)

and (f) $-O-\underset{\underset{O}{||}}{C}-CH=CH-\underset{\underset{O}{||}}{C}-O-CH_2-\underset{\underset{OH}{|}}{CH}-CH_2-O-\underset{\underset{O}{||}}{C}-CH=CH_2$, (VI)

with the proviso that only one $R^1$ can be —OH or a radical of Formula III, IV, or VI, one or more organic peroxides, and one or more customary adjuvant substances.

2. The composition of claim 1 which comprises up to 50 percent by weight, based upon the total weight of the composition, of additional polymerizable components.

3. The composition of claim 1, wherein the organic peroxides are hydroperoxides.

4. The composition of claim 1 which contains one or more customary adjuvant substances selected from stabilizers, accelerators, plasticizers, inorganic fillers, thickeners, dyes, or mixtures thereof.

5. The composition of claim 4 which contains quinone or hydroquinone as stabilizer.

6. The composition of claim 4 which contains an imide or sulfohydrazide accelerator.

7. The composition of claim 6, wherein the accelerator is benzoic acid sulfimide or p-toluene sulfonic acid hydrazide in combination with a tertiary amine.

8. The composition of claim 4 which contains one or more fillers selected from the group consisting of finely-divided silicon dioxide, silicates, bentonites, calcium carbonate, and titanium dioxide.

* * * * *